(12) United States Patent  (10) Patent No.: US 7,807,445 B2
Basilio et al.                  (45) Date of Patent:    Oct. 5, 2010

(54) ANTIBIOTIC COMPOUND

(75) Inventors: Angela Basilio, Madrid (ES); Olga Genilloud, Madrid (ES); Hiranthi Jayasuriya, Edison, NJ (US); Ignacio Gonzalez, Madrid (ES); Sheo B. Singh, Edison, NJ (US); Oscar Salazar, Madrid (ES); Jun Wang, Millburn, NJ (US)

(73) Assignees: Merck Sharp and Dohme de Espana, S.A., Madrid (ES); Merck Sharp & Dohme Corp., Rahway, NJ (US)

( * ) Notice: Subject to any disclaimer, the term of this patent is extended or adjusted under 35 U.S.C. 154(b) by 954 days.

(21) Appl. No.: 11/587,074

(22) PCT Filed: May 20, 2005

(86) PCT No.: PCT/US2005/017832

§ 371 (c)(1),
(2), (4) Date: Oct. 20, 2006

(87) PCT Pub. No.: WO2005/115400

PCT Pub. Date: Dec. 8, 2005

(65) Prior Publication Data

US 2010/0144879 A1    Jun. 10, 2010

Related U.S. Application Data

(60) Provisional application No. 60/573,899, filed on May 24, 2004.

(51) Int. Cl.
  *A61K 39/10*  (2006.01)
  *A61K 31/195* (2006.01)
  *C07C 229/00* (2006.01)
(52) U.S. Cl. .................... 435/253.5; 562/455; 514/559; 514/567

(58) Field of Classification Search ............... 562/450, 562/455; 514/557, 558, 559, 567; 424/252.35
See application file for complete search history.

(56) References Cited

U.S. PATENT DOCUMENTS 2,891,091 A    6/1959    Darrach et al.

FOREIGN PATENT DOCUMENTS

WO    2005/009391    2/2005

OTHER PUBLICATIONS

F. D. Lowry "Antimicrobial Resistance: The Examply of *Staphylococcus aureus*", 2003, pp. 1265-1273, vol. 111, No. 9, J. of Clinical Investigation.

(Continued)

*Primary Examiner*—Taylor Victor Oh
(74) *Attorney, Agent, or Firm*—Sylvia A. Ayler; Baerbel R. Brown; John C. Todaro

(57) ABSTRACT

Fermentation of a nutrient medium with a eubacterium *Streptomyces* sp. yields a novel antibacterial compound of structural formula (I).

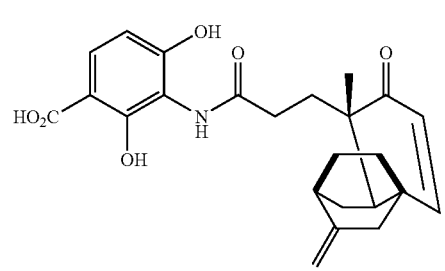

5 Claims, 2 Drawing Sheets

OTHER PUBLICATIONS

E. B. Shirling et al., "Methods for Characterization of *Stretomyces* Species", 1966, pp. 313-340, vol. 16, No. 3, International Journal of Systematic Bacteriology.

Thompson, "Antimalarial activity of beta-resorcylic acid and analogs . . . ", Antibiotics and Chemotherapy (1953), vol. 3, pp. 399-408.

Wang, "Discovery of platencin, a dual FabF and FabH inhibitor . . . ", PNAS (2007), vol. 104, pp. 7612-7616.

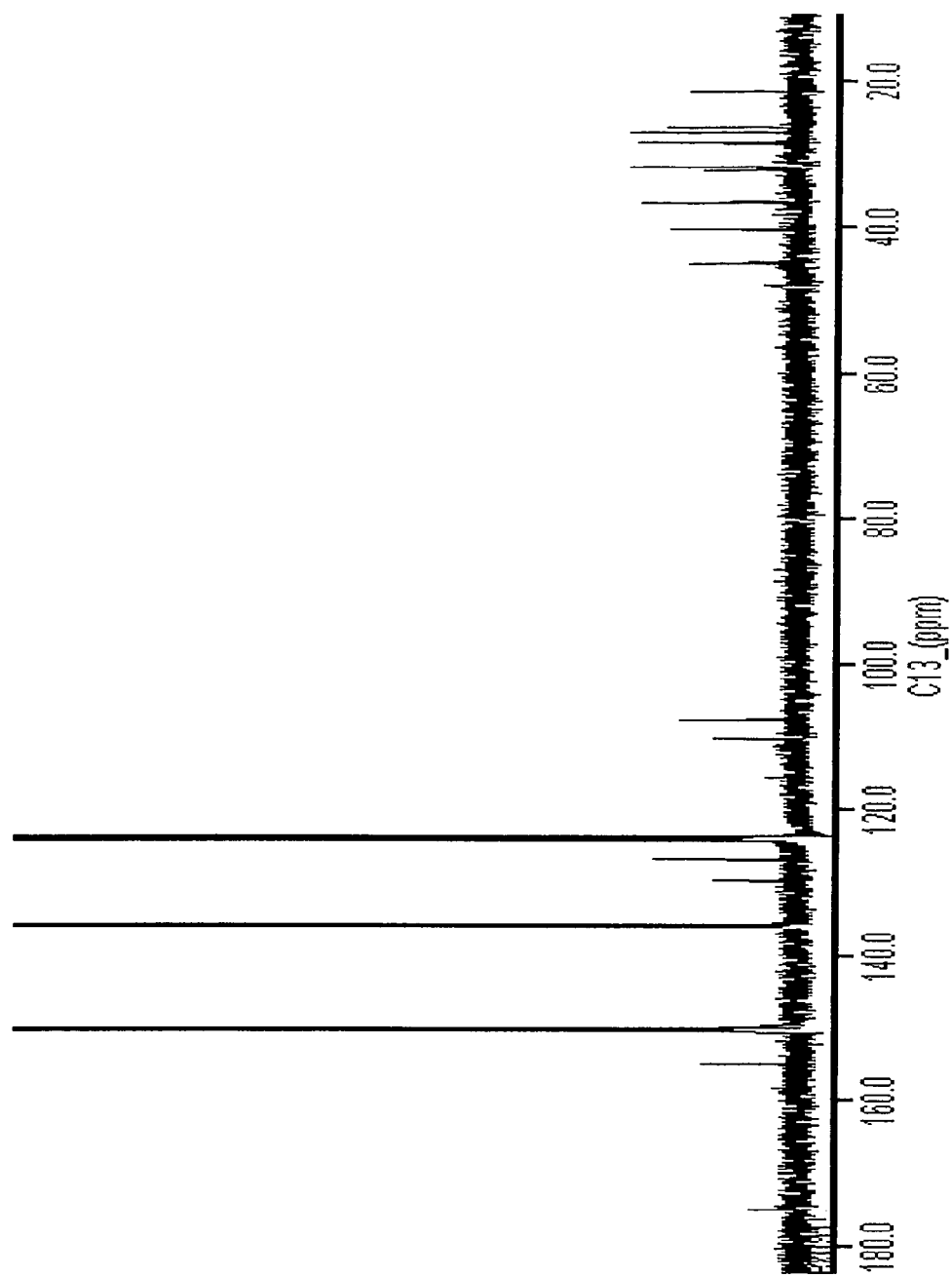
FIGURE 1 is a 13C NMR spectrum of Compound I in C5D5N.

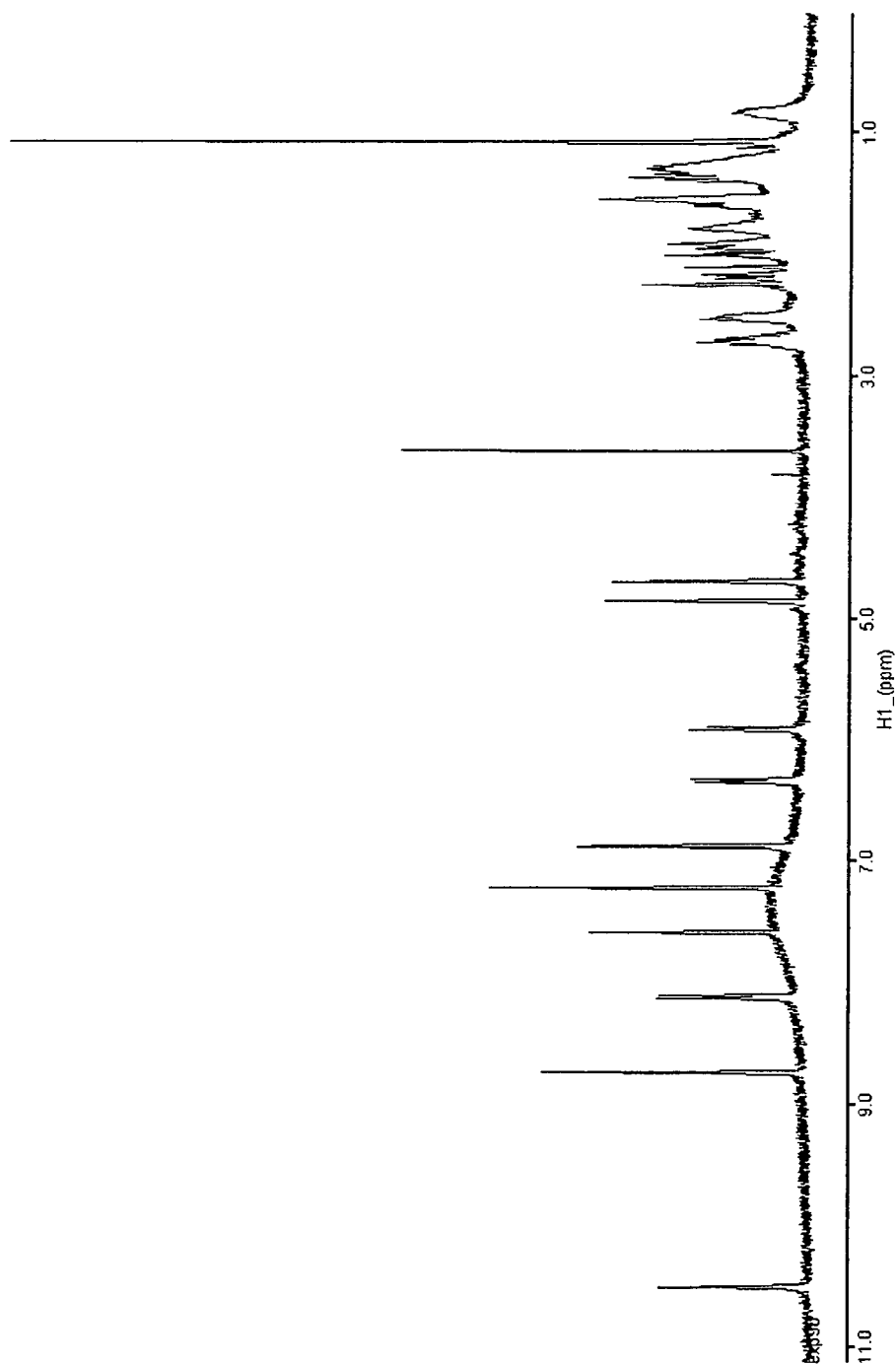
FIGURE 2 is a $^1$H NMR spectrum of Compound I in $C_5D_5N$.

ANTIBIOTIC COMPOUND

This Application claims the benefit of U.S. Provisional Application 60/573,899, filed May 24, 2004.

BACKGROUND OF THE INVENTION

The present invention relates to a novel natural product that possesses antibacterial activity.

Infections caused by bacteria are a growing medical concern as many of these pathogens are resistant to various common antibiotics. Such microbes include *Staphylococcus aureus, Staphylococcus epidermidis, Staphylococcus hemolyticus, Streptococcus pyogenes, Streptococcus pneumoniae, Enterococcus faecalis, Enterococcus faecium, Pseudomonas aeruginosa, Actinobacter calcoaeticus, Escherichia coli* and *Stenotrophomonas maltophilia*. The antibiotic of this invention comprises an important contribution to therapy for treating infections that are resistant to various known antibiotics. For a review see: F. D. Lowy *The Journal of Clinical Investigation* 2003, 111 (9), 1265.

In the present invention, a novel natural product isolated from the eubacterial fermentation of *Streptomyces* sp. is described. This compound displays antibacterial activity against various pathogens, many of which have demonstrated resistance to currently available antibiotics.

SUMMARY OF THE INVENTION

This invention describes the novel natural product shown in formula I and its use as an antibacterial agent:

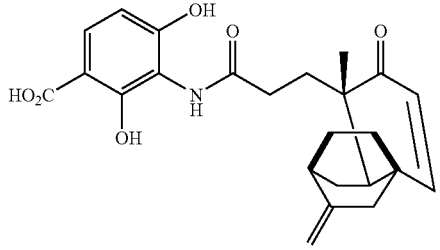

I or a pharmaceutically acceptable salt thereof which is effective in the treatment of bacterial infections.

The invention is also concerned with a process for the production of Compound I by fermentation with the eubacterium, *Streptomyces* sp. The invention is also concerned with a process for isolating the compounds of Formula I from fermentation broths.

BRIEF DESCRIPTION OF THE DRAWINGS

FIG. 1 is a $^{13}C$ NMR spectrum of Compound I in $C_5D_5N$.
FIG. 2 is a $^1H$ NMR spectrum of Compound I in $C_5D_5N$.

DETAILED DESCRIPTION OF THE INVENTION

This invention describes the compound of structural formula I:

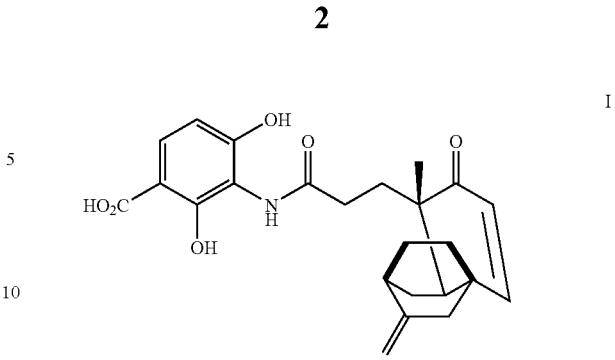

I or a pharmaceutically acceptable salt thereof.

The pharmaceutically acceptable salts of the compound of this invention include the conventional non-toxic salts as formed, from non-toxic inorganic or organic bases. For example, such conventional non-toxic salts include those derived from inorganic bases such as an alkali or alkaline earth metal hydroxide, e.g., potassium, sodium, lithium, calcium, or magnesium, and the like: and the salts prepared from organic bases such as an amine, e.g., dibenzylethylene-diamine, trimethylamine, piperidine, pyrrolidine, benzylamine and the like, or a quaternary ammonium hydroxide such as tetramethylammonium hydroxide and the like.

The pharmaceutically acceptable salts can be synthesized from the compounds of this invention by conventional chemical methods. Generally, the salts are prepared by reacting the free acid with stoichiometric amounts or with an excess of the desired salt-forming inorganic or organic base in a suitable solvent or various combinations of solvents.

Compound I of this invention displays antibiotic activity useful in the treatment of bacterial infections. It demonstrates antibacterial activity against various strains of *S. aureus, S. pneumoniae, E. faecalis, E. faecium, B. subtilis* and *E. coli* including species that are resistant to many known antibiotics such as methicillin-resistant *S. aureus* (MRSA), vancomycin-resistant *Enterococcus* sp. (VRE), multidrug-resistant *E. faecium*, macrolide-resistant *S. aureus* and *S. epidermidis*, and linezolide-resistant *S. aureus* and *E. faecium*.

The compound of this invention can be formulated in pharmaceutical compositions by combining Compound I with a pharmaceutically acceptable carrier. Examples of such carriers are set forth below.

The compound may be employed in powder or crystalline form, in liquid solution, or in suspension. It may be administered by a variety of means; those of principal interest include topically, orally and parenterally by injection (intravenously or intramuscularly).

Compositions for injection, one route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the Compound, the virulence of the infection and other factors. Such matters, however, are left to the routine discretion of the physician according to principles of treatment well known in the antibacterial arts.

The compositions for administration to humans per unit dosage, whether liquid or solid, may contain from about 0.01% to as high as about 99% of Compound I, one embodiment of the range being from about 10-60%. The composition will generally contain from about 15 mg to about 2.5 g of Compound I, one embodiment of this range being from about 250 mg to 1000 mg. In parenteral administration, the unit dosage will typically include pure Compound I in sterile water solution or in the form of a soluble powder intended for solution, which can be adjusted to neutral pH and isotonicity.

The invention described herein also includes a method of treating a bacterial infection in a mammal in need of such treatment comprising the administration of Compound I to the mammal in an amount effective to treat the infection.

One embodiment of the methods of administration of Compound I includes oral and parenteral methods, e.g., i.v. infusion, i.v. bolus and i.m. injection.

For adults, about 5-50 mg of Compound I per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000-2000 mg three to four times daily may be recommended.

For children, a dose of about 5-25 mg/kg of body weight given 2, 3, or 4 times per day is preferred; a dose of 10 mg/kg is typically recommended.

Another aspect of this invention is the process for producing Compound I, which comprises cultivating a *Streptomyces* sp. microorganism in a suitable nutrient medium and then recovering the compound of this invention from the fermentation broth. The *Streptomyces* sp. microorganism, ATCC# PTA-5942 identified as the eubacterium *Streptomyces* sp. with the following taxonomic studies is deposited in the Merck Culture Collection as MA7339.

The organism was subsequently placed on permanent deposit with the Amercian Type Culture Collection (ATCC), 12301 Parklawn Drive, Rockville, Md., 20852 and have been assigned accession number ATCC# PTA-5942 (Merck# MA7339).

Any restrictions relating to public access to the microorganism shall be irrevocably removed upon patent issuance. Although the use of these particular species is described in connection with this invention, there may be other species and mutants of the above organism capable of producing Compound I, and their use is contemplated in carrying out the process of this invention.

The compound of structural Formula I is produced by the aerobic fermentation of a suitable medium under controlled conditions via inoculation with a culture of the eubacterium, *Streptomyces* sp. The suitable medium is preferably aqueous and contains sources of assimilable carbon, nitrogen, and inorganic salts.

The medium employed for fermentation by the *Streptomyces* sp. is primarily the well-known Difco Tryptic Soy Broth, either alone or with added nutrients commonly used by those skilled in the art.

It should be noted that the nutrient media described herein are merely illustrative of the wide variety of media which may be employed and are not intended to limit the scope of this invention in any way.

The fermentation is conducted at temperatures ranging from about 10° C. to about 40° C.; however for optimum results it is preferred to conduct the fermentation at about 28° C. The pH of the nutrient medium during the fermentation can be about 5.5 to about 7.5.

It is to be understood that for the fermentative production of the compound of this invention, the invention is not limited to the use of the particular *Streptomyces* sp. with ATCC accession number, ATCC# PTA-5942 (Merck# MA7339). It is especially desired and intended that there be included in the scope of this invention the use of other natural or artificial mutants produced or derived from the described cultures, or other variants or species of the *Streptomyces* genus insofar as they can produce the compound of this invention. The artificial production of mutant species or strains of *Streptomyces* from ATCC# PTA-5942 (Merck# MA7339) may be achieved by conventional, physical or chemical mutagens, for example, ultraviolet irradiation of the described culture, or nitrosoguanidine treatment and the like. Recombinant DNA techniques such as protoplast fusion, plasmid incorporation, chromosome fragment incorporation and the like also may prove useful.

EXAMPLE 1

Production of Compound I—

| SEED Media composition: | |
| --- | --- |
| Component | g/L |
| Soluble starch | 20 |
| Dextrose | 10 |
| NZ Amine type E | 5 |
| Difco Beef Extract | 3 |
| Bacto (Difco) Peptone | 5 |
| Difco Yeast Extract | 5 |
| CaCO3 | 1 | pH 7.0

| YME.TE (Production Medium, g/l) | |
| --- | --- |
| Media Component | g/L |
| *Difco yeast extract | 6 |
| *Malt extract | 15 |
| *Dextrose | 6 |
| Trace Elements | 5 ml |
| MOPS | 20 | pH = 7.0

A frozen suspension (1.3 mL) of a *Streptomyces* sp. ATCC# PTA-5942 (MA7339) was inoculated into a 250 mL flask containing 50 mL of seed medium. The flask was incubated at 28.0° C. with an agitation of 220 RPM for 48 hours. The second stage seed was developed by transferring 3% inoculum of the first stage seed into a 250 ml shake flask containing 50 mL of seed medium. The flask was incubated at 28.0° C. with an agitation of 220 RPM for 24 hours. A 5% inoculum of the second stage seed was transferred to 30ml of YME-TE in a 250ml and incubated at 32.0° C. with an agitation of 220 RPM for 12 days.

Isolation of Compound I:

To a two liter fermentation broth was added two liter of acetone and shaken on a shaker for two hours and filtered. The filtrate was concentrated under reduced pressure to remove most of the acetone and charged on to a 75 mL amberchrome (CG161s) column. The column was eluted with a gradient of 90% water to 100% methanol that eluted the compound in a borad zone which upon concentration and lyophilization afforded 170 mg of semi-purified fraction. A 80 mg portion of the fraction was purified by prep HPLC (Zorbax Rx C8 21.4× 250 mm with a gradient of 20-98% aqueous acetonitrile containing 0.1% trifluoroacetic acid to produce 1.1 mg of compound I. The structure was elucidated by spectroscopic analysis (see below).

Physical Data of Compound I:

TABLE

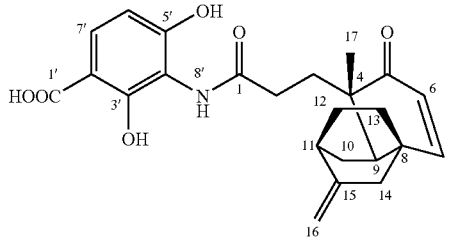

| MW | 425 |
|---|---|
| MF | $C_{24}H_{27}NO_6$ |
| HEESIFTMS | Found: 426.1911; calcd for M + H: 426.1911 |
| $[\alpha]^{23}_D$ | +2.1° (c 0.96, $CH_3OH$) |
| UV ($CH_3OH$) $\lambda_{max}$ | 226 (ε 16,837) 296 (2,663) nm |

$^1$H and $^{13}$C NMR Assignment of Compound I at 500 MHz

| # | $C_5D_5N^{13}{}_C$ | Type | $C_5D_5N^1{}_H$ |
|---|---|---|---|
| 1 | 175.2 | C° | |
| 2 | 32.2 | $CH_2$ | 2.70, m |
| 3 | 31.8 | $CH_2$ | 2.53, m |
|   |      |       | 1.92, m |
| 4 | 48.1 | C° | |
| 5 | 204.1 | C° | |
| 6 | 126.8 | CH | 5.92, d, 10.0 |
| 7 | 154.9 | CH | 6.36, d, 10.0 |
| 8 | 36.7 | C° | |
| 9 | 40.4 | CH | 2.00, t, 10.2 |
| 10 | 27.1 | $CH_2$ | 1.60, m |
|    |      |        | 1.36, brt, 10.2 |
| 11 | 36.6 | CH | 2.26, m |
| 12 | 26.5 | $CH_2$ | 1.78, m |
|    |      |        | 1.56, m |
| 13 | 28.5 | $CH_2$ | 1.56, t, 7.8 |
|    |      |        | 1.80, m |
| 14 | 44.9 | CH | 1.93, d, 10.2 |
|    |      |    | 2.15, d, 10.2 |
| 15 | 149.8 | C° | |
| 16 | 107.8 | $CH_2$ | 4.71, brs |
|    |       |        | 4.87, brs |
| 17 | 21.5 | $CH_3$ | 1.09, s |
| 1' | 175.2 | C° | |
| 2' | 107.6 | C° | |
| 3' | 158.8 | C° | |
| 4' | 115.8 | C° | |
| 5' | 158.3 | C° | |
| 6' | 110.4 | CH | 6.88, d, 8.4 |
| 7' | 129.8 | CH | 8.12, d, 8.4 |
| 8' |       | NH | 10.50, s |
| 3'-OH | | | |
| 5'-OH | | | |

Characterization of Culture

General description of culture MA-7339 producer of compound I is described. Observations of growth, general cultural characteristics and carbon source utilization were made in accordance with the methods of Shirling and Gottlieb (*Int. J. Syst. Bacteriol.* (1966) 16: 313-340). Coloration of the cultures was determined by comparison with color standards contained in the Methuen Handbook of Colour (A. Kornerup and J. H. Wauscher, Third Edition, 1978).

Chemical composition of the cells was determined using the methods of Lechevalier and Lechevalier (1980).

Fatty acid composition was determined using a modified sample preparation (Sasser, 1990). Analysis of fatty acid methyl esters (FAMEs) was carried out by capillary gas chromatography using a Hewlett Packard Model 6890N gas chromatograph/Microbial Identification System software (MIDI, Inc., Newark, Del) equipped with a phenyl methyl silicone column (0.2 mm×25 m). Individual fatty acids identification was determined by the Microbial Identification System software.

The complete 16S rDNA sequence was determined from the 1500 by PCR fragment obtained using primers 27f and 1525r (Lane, 1991). The PCR product was used as template in sequencing reactions using an ABI PRISM™ Dye Terminator Cycle sequencing Kit (Perkin Elmer). Partial sequences were assembled using the GCG Fragment Assembly System (Wisconsin Package, version 8) and sequences were aligned with the program CLUSTALW (Intelligenetics, Inc.). The phylogenetic analysis of the aligned sequences was performed using the maximum-parsimony analysis with the branch-and-bound algorithm of the Phylogeny Using Parsimony Analysis (PAUP) program version 4.0. (Swofford, 1993).

Source:

Strain MA7339 was obtained from a soil collected in Mallorca, Balearic Islands, Spain. The strain was isolated after pretreatment of the soil with 1% (w/v) chloramine T and plating on humic-acid based agar supplemented with 20 ug/ml nalidixic acid. After purification on Yeast Malt Extract agar, the isolate was detected active when tested as agar plug in the FabF_SPAR_C screen.

General Growth Characteristics.

Strain MA7339 grows well on a range of agar media such as Yeast Malt Extract, Oatmeal, Glycerol Asparagine, Inorganic Salts Starch and Trypticase Soy agars at 28° C. The gross colonial morphology is typical of streptomycetes and its growth characteristics, including spore-mass colour, substrate mycelial pigmentation and the production of different pigments were recorded in different agar media (Table 1).

Colony morphology (on Yeast Malt Extract Agar, ISP2): Substrate mycelium initially whitish yellow turns yellowish brown (5D7) after 21 days of incubation. The initial white aerial mycelium continues to develop after 21 days incubation turning whitish grey (5E1/5E2) with brownish wet exudate droplets.

Micromorphology: the spore-chain morphology was examined directly on the plates by light microscopy under 400× and 1000× magnification. Observations were made after 7, 14 and 21 days of cultivation on Yeast Malt Extract agar. The aerial mycelium arises from extensive branched substrate hyphae. Sparse branched aerial hyphae differentiate initially into short and irregularly tight coiled spore chain spirals. Sporophores are formed by less than 10-20 spores and with time tend to coalesce in a dark mucous mass of spores in older cultures. Similar morphologies were observed in most of the other test media but with different degrees of coalescence. On the contrary in the glycerol asparagine agar the strain grows as a sterile vegetative mycelium.

and the *S. platensis* strains MA7327 and MA7331. A phylogenetic tree based on these 16S rDNA sequences was built using the maximum parsimony method. Bootstrap replicates from each grouping was used as a measure of statistical confidence. A grouping found on 95% of bootstrap replicates was considered statistically significant.

The strain MA7339 is associated to the strain *Streptomyces platensis* ATCC 13865 and the strains MA7327 and MA7331. This close relationship is highly supported by the bootstrapping value (97%) and suggests that this isolate can be identified as another strain of the species *Streptomyces platensis* (FIG. 2).

TABLE 1

Cultural characteristics of *Streptomyces* sp. MA7339 (21 days, 28° C.)

| Medium | Amount of growth | Aerial Mycelium | Soluble pigments | Substrate Mycelium |
|---|---|---|---|---|
| Yeast Extract Malt Extract (ISP2) | Abundant | Whitish grey (5E1/5E2), dense growth, extensive aerial mycelium with short and tight irregular spore chains forming loops and coils. Sporophores born in main and secondary aerial branches, coalescence. | None | Yellowish brown (5D7) |
| Oatmeal (ISP3) | Abundant | Grey (5E2/F2), extensive aerial mycelium, coalescence of tight coiled spore chains. | None | Olive brown (4E3) |
| Inorganic Salts Starch (ISP4) | Abundant | Greyish brown (5D3/F3), extensive aerial mycelium, coalescence of chains. | None | Light yellow (4A4) |
| Glycerol Asparagine (ISP5) | Sparse | none | None | Greyish orange(5B4), sterile substrate mycelium |
| Tyrosine Agar (ISP7) | Abundant | Orange grey (5B2), extensive aerial mycelium growth, short and tight spirals in aerial hyphae, collapsing in coalescence and knots | none | Dark brown (6F7) |

Chemotaxonomic Analysis.

The analysis of cell wall composition shows that strain MA7339 contains LL-A2pm in whole-organism hydrolysates, a characteristic of *Streptomyces*, and glucose and ribose as major cell wall sugars. The strain is rich in saturated straight-chain and iso- and anteiso- fatty acids and whole-cell methanolysates contain the predominant fatty acids 15:0 anteiso (12.43%) and 16:0 iso (17.94%), which are also typical of *Streptomyces*. Nevertheless the major component is the fatty acid species 15:0 iso (20.43%). A complete fatty acid composition is given in Table 2.

All these chemotaxonomic analyses indicate that the strain corresponds to a member of the genus *Streptomyces*.

Physiological Properties.

Strain MA7339 presents the following carbon utilization pattern (Table 3):

good utilization of sucrose, D-xylose, D-fructose and raffinose; moderate utilization of D-glucose, I-inositol, and D-mannitol; and no utilization of L-arabinose, cellulose and rhamnose.

16S rDNA Sequence and Phylogenetic Analysis.

The complete 16S rDNA sequence has been determined for strain MA-7339 (FIG. 1). Sequence was aligned with *Streptomyces* nucleotide sequences from Genbank (AB045882)

TABLE 2

Major fatty acids found in strain MA7339.

| Fatty acid | % of total fatty acids |
|---|---|
| 14:0 iso | 5.66 |
| 15:0 iso | 20.43 |
| 15:0 anteiso | 12.43 |
| 15:0 anteiso 2OH | 8.00 |
| 15:0 | 3.48 |
| 16::0 | 2.52 |
| 16:0 iso | 17.94 |
| 16:1 iso H | 3.54 |
| 16:0 iso 2OH | 1.14 |
| 17:0 anteiso | 3.58 |
| 17:0 cyclo | 1.48 |
| 17:0 iso | 3.36 |
| 17:1 iso C | 2.28 |
| 17:1 anteiso C | 2.28 |

TABLE 3

Carbohydrate utilization patterns of strains MA7339.

| Carbon source | Growth levels |
|---|---|
| D-glucose | 2 |
| L-arabinose | 0 |
| Sucrose | 3 |
| D-xylose | 3 |
| I-inositol | 2 |
| D-mannitol | 2 |
| D-fructose | 3 |
| Rhamnose | 0 |
| Raffinose | 3 |
| Cellulose | 0 |

Growth on the following compounds as sole carbon sources; Observations were made at 7, 14 and 21 days, 28° C.; Growth levels: 3 = good utilization; 2 = moderate utilization; 1 = poor utilization; 0 = no utilization.

FIG. 1. 16S rDNA sequences of strain MA7339.

```
Strain MA7339 16S rDNA region (from: 1 to: 1445)
   1 CCTCCTTCGG GAGGGGATTA GCTGGCGAAC GGGTGAGTAA CACGTGGGCA
  51 ATCTGCCCTT CACTCTGGGA CAAGCCCTGG AAACGGGGTC TAATACCCGG
 101 ATACGACACA CGACCGCATG GTCTGTGTGT GGAAAGCTCC GGCGGTGAAG
 151 GATGAGCCCG CGGCCTATCA GCTTGTTGGT GGGGTGATGR CCTACCAAGG
 201 CGACGACGGG TAGCCGGCCT GAGAGGGCGA CCGGCCACAC TGGGACTGAG
 251 ACACGGCCCA GACTCCTACG GGAGGCAGCA GTGGGGAATA TTGCACAATG
 301 GGCGAAAGCC TGATGCAGCG ACGCCGCGTG AGGGATGACG GCCTTCGGGT
 351 TGTAAACCTC TTTCAGCAGG GAAGAAGCGA GAGTGACGGT ACCTGCAGAA
 401 GAAGCGCCGG CTAACTACGT GCCAGCAGCC GCGGTAATAC GTAGGGCGCA
 451 AGCGTTGTCC GGAATTATTG GGCGTAAAGA GCTCGTAGGC GGCTTGTCAC
 501 GTCGGATGTG AAAGCCCGGG GCTTAACCCC GGGTCTGCAT TCGATACGGG
 551 CAGGCTAGAG TTCGGTAGGG GAGATCGGAA TTCCTGGTGT AGCGGTGAAA
 601 TGCGCAGATA TCAGGAGGAA CACCGGTGGC GAAGGCGGAT CTCTGGGCCG
 651 ATACTGACGC TGAGGAGCGA AAGCGTGGGG AGCGAACAGG ATTAGATACC
 701 CTGGTAGTCC ACGCCGTAAA CGTTGGGAAC TAGGTGTGGG CGACATTCCA
 751 CGTCGTCCGT GCCGCAGCTA ACGCATTAAG TTCCCCGCCT GGGGAGTACG
 801 GCCGCAAGGC TAAAACTCAA AGGAATTGAC GGGGCCCGC ACAAGCAGCG
 851 GAGCATGTGG CTTAATTCGA CGCAACGCCA AGAACCTTA CCAAGGCTTG
 901 ACATACACCG GAAACGTCTG GAGATCAGGC GCCCCTTGT GTCCGGTGTA
 951 TCATGGTGGT GCATGGCTGT CGTCAGCTCG TGTCGTGAGA TGTTGGGGTT
1001 TAAKTCCCCG CAACGAGCGC AACCCTTGTT CTGTGTTGCC AGCATGCCCT
1051 TCGGGGTGAT GGGGACTCAC AGGAGACTGC CGGGGTCAAC TCGGAGGAAG
1101 GTGGGGACGA CGTCAAGTCA TCATGCCCCT TATGTCTTGG GCTGCACACG
1151 TGCTACAATG GCCGGTACAA TGAGCTGCGA TACCGCGAGG TGGAGCGAAT
1201 CTCAAAAAGC CGGTCTCAGT TCGGATTGGG GTCTGCAACT CGACCCCATG
1251 AAGTCGGAGT TGCTAGTAAT CGCAGATCAG CATTGCTGCG GTGAATACGT
1301 TCCCGGGCCT TGTACACACC GCCGGTCACG TCACGAAAGT CGGTAACACC
1351 CGAAGCCGGT GGCCCAACCC CTTGTGGGAG GAATCGTCG AAGGTGGGAC
1401 TGGCGATTGG GACGAAGTCG TAACAAGGTA GCCGTACCGG AAGGT
```

The protocols used to determine the antibacterial activity of Compound I are described below.

Materials:
Cation-Adjusted Mueller Hinton Broth (MH; BBL)
50% Lysed Horse Blood (LHB; BBL) (stored frozen)

0.9% Sodium Chloride (Saline; Abbott Labs): Received prepared from manufacturer.

2× Skim Milk (Remel): Received prepared from manufacturer.

All agar plates are received prepared from manufacturer.

| Conditions and Inoculum for Representative Strains | |
|---|---|
| Bacillus, Staphylococcus, Enterococcus: | Incubation Conditions, 35° C.; MICs read at 18-22 hours; |
| Escherichi:, | Cation-Adjusted Mueller Hinton (CAMHB; BBL); Inoculum = $10^5$ CFU/mL |
| Strep. pneumoniae: | Incubation Conditions, 35° C.; MICs read at 22-24 hours; Cation-Adjusted Mueller Hinton + 2.5% Lysed Horse Blood (LHB); Inoculum = $10^5$ CFU/mL |
| Haemophilus influenzae: | Incubation Conditions, 35° C.; MICs read at 18-22 hours; Haemophilus Test Medium (HTM; Remel); Inoculum = $10^5$ CFU/mL |
| Candida: | Incubation Conditions, 35° C.; MICs read at 24 hours; RPMI 1640 Medium (BioWhittaker) Inoculum = $10^3$ CFU/mL |

Highest Concentration of Antibiotic Tested = 64 μg/mL (when starting from a 1 mg/mL sol'n in 50% DMSO)
Final Concentration of DMSO per well = 3.2%

RPMI 1640 (BioWhittaker)
Human Serum (Pel-Freez)
RPMI 1640 (BioWhittaker)
Haemophilus Test Medium (HTM, Remel)
Trypticase Soy Broth (TSB, 5 mL/tube; BBL)
0.9% Sodium Chloride (Saline; Baxter)
Trypticase Soy+5% Sheep Blood Agar Plates (TSA; BBL)
Sabouraud Dextrose Agar Plates (BBL)
Chocolate Agar Plates (BBL)
2× Skim Milk (Remel)
Microbank Beads (Kramer Scientific)
MIC 2000 Microtiter plate inoculator.
2× Trypticase Soy Broth (TSB, BBL)+15% glycerol/50% horse serum.
96-Well Microtiter plates, lids, inoculum trays (Dynex Laboratories)
8-Channel Finn Multichannel pipettor, 0.5-10 μL volume Methods:

Media Preparation

Cation-Adjusted Mueller Hinton Broth (BBL): Prepared according to manufacturer's instructions (22 gms dissolved in 1000 mL water; autoclaved 22 minutes). Stored refrigerated. Filter-sterilized before use using a Corning 0.45 Tm cellulose acetate filter.

50% Lysed Horse Blood: Defibrinated horse blood is diluted 1:1 with sterile distilled water; frozen, thawed and re-frozen (at least 7 times), then centrifuged. Stored frozen at −20° C.

Cation-Adjusted Mueller Hinton+2.5% Lysed Horse Blood: Aseptically add 5 mL 50% lysed horse blood to 100 mL Cation-Adjusted Mueller Hinton Broth. Filter-sterilize before use using a Corning 0.45 Tm cellulose acetate filter.

Cation-Adjusted Mueller Hinton+50% Human Serum: Aseptically add 50 mL Human Serum to 50 mL 2× Cation-Adjusted Mueller Hinton Broth. Filter-sterilize before use using a Corning 0.45 Tm cellulose acetate filter.

Haemophilus Test Medium (Remel): Received prepared from manufacturer. Filter-sterilize before use using a Corning 0.45 Tm cellulose acetate filter.

Selection and Maintenance of Isolates

The strains used are isolates from either the Merck Culture Collection, or from Clinical Trials. The strain of *Haemophilus influenzae* is a mouse pathogen used for in vivo testing at Merck. The *Escherichia coli* strain is a cell wall permeable strain. The *Candida albicans* strain is used as a control. These culture are maintained as frozen stocks at −80° C. in a.) Microbank beads; b.) 2× Skim Milk; or c.) in 2× Trypticase Soy Broth+15% glycerol/50% horse serum (*Haemophilus* and *Streptococcus pneumoniae*).

Inoculum Preparation

Selected isolates are subcultured onto either Chocolate Agar Plates (*Haemophilus influenzae*), onto Trypticase Soy+5% Sheep Blood Agar Plates (*Streptococcus pneumoniae, Staphylococcus aureus, Escherichia coli, Enterococcus, Bacillus*) or onto Sabouraud Dextrose Agar (*Candida*) and incubated at 35° C. *Haemophilus* and *Streptococcus pneumoniae* are incubated in 5% $CO_2$; all other isolates are incubated in ambient air. Isolates are subcultured 2× before assay.

Colonies are selected from plates and used to prepare an inoculum equivalent to a 0.5 McFarland standard in Trypticase Soy Broth. An inoculum with a density equivalent to a 1.0 McFarland standard is prepared for *Streptococcus pneumoniae*. The inoculum density for all cultures is ~$10^8$ CFU/mL in TSB. This TSB inoculum is diluted 1:10 in sterile saline (4 mL inoculum+36 mL saline; equivalent to ~$10^7$ CFU/mL) and kept on ice until used to inoculate microtiter plates.

Colony counts are performed on randomly-selected isolates to confirm CFU/well (TSB inoculum plated out $10^{-5}$, $10^{-6}$ onto either TSA II+5% SB or onto chocolate agar plates, incubated overnight, 35° C., $CO_2$)

Plate Filling

All wells of 96-well microtiter plates (Dynex) are filled with 100 TL media. Haemophilus test media plates are prepared to test *Haemophilus influenzae*; Cation-Adjusted Mueller Hinton+5% Lysed Horse Blood plates are prepared to test *Streptococcus pneumoniae*; Cation-Adjusted Mueller Hinton Broth plates are prepared to test *Enterococcus, Sta-*

*phylococcus aureus, Escherichia col* and *Bacillus subtilis*. RPMI 1640 is used to test *Candida*. The MICs against *S. aureus* Smith are determined in Cation-adjusted Mueller Hinton and in Cation-Adjusted Mueller Hinton+50% Human Serum, to determine if the compound is inactivated by some component in serum (indicated by an increase in the MIC). Filled plates are wrapped in plastic bags (to minimize evaporation), stored frozen and thawed before use.

Preparation of Compounds

The compounds are prepared on a weight basis. Compounds are prepared to 2 mg/mL in 100% DMSO, then diluted to 1 mg/mL in a 1:1 dilution of DMSO/2× CAMHB (final concentration=50%DMSO/50% CAMHB). Compounds are serially diluted 1:1 in 50% DMSO/50% CAMHB in BD Biosciences Deep Well Polypropylene 96 well plates (starting concentration 1 mg/mL).

Microbroth Dilution Assay

Using a Finn Automated Multichannel Pipette, (0.5-10 μL volume) 6.4 TLs of antimicrobial working solutions are added to wells of filled microtiter plates (concentration of antimicrobial in first well=64 μg/mL; concentration of DMSO=3.2%). Antimicrobials are added in this manner to keep constant the amount of DMSO in each well (to keep compounds solubilized and to account for the possibility of non-specific killing by the DMSO. The last row contains a growth control of 3.2% DMSO.

With each assay, controls are run. They are Penicillin G and Chloramphenicol, prepared in the same manner as the compounds. Ertapenem is included as a control for the serum protein binding assay.

Plate Inoculation

All wells of microtiter plates are inoculated with (saline-diluted) culture using the MIC 2000 System, an automated plate inoculating device which delivers an inoculum of 1.5 TL per well. Plates are incubated at 35° C. in ambient air. An uninoculated plate is also incubated as a sterility check. Results are recorded after 22-24-hours' incubation. Plates were read to no growth. The MIC is defined as the lowest antimicrobial level which resulted in no growth after 22-24-hours' incubation.

Compound I demonstrates antibacterial activity against various strains of *S. aureus, S. pneumoniae, E. faecalis, E. faecium, B. subtilis* and *E. coli*. Compound I also demonstrates antibacterial activity against various species that are resistant to many known antibiotics such as methicillin-resistant *S. aureus* (MRSA), vancomycin-resistant *Enterococcus* sp. (VRE), multidrug-resistant *E. faecium*, macrolide-resistant *S. aureus* and *S. epidermidis*, and linezolid-resistant *S. aureus* and *E. faecium*. The minimum inhibitory concentration (MIC) values for these test strains range from 0.5 to 32 ug/mL. MICs are obtained in accordance to the NCCLS guidelines.

What is claimed is:

1. An isolated compound of structural formula (I);

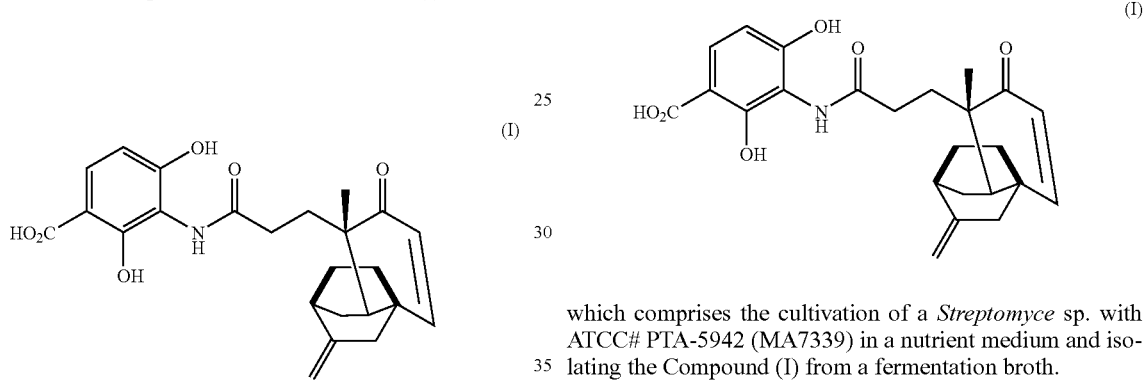

or a pharmaceutically acceptable salt thereof.

2. A process for the preparation of an isolated compound of structural formula (I): which comprises the cultivation of a *Streptomyce* sp. with ATCC# PTA-5942 (MA7339) in a nutrient medium and isolating the Compound (I) from a fermentation broth.

3. The process of claim 2 wherein the fermentation is conducted at a temperature of about 10° C. to about 40° C.

4. The process of claim 3, wherein the fermentation is conducted at a temperature of about 28° C.

5. A pharmaceutical composition comprising a pharmaceutically acceptable carrier and an effective amount of a compound of structure (I) of claim 1.

* * * * *

```
SEQUENCE LISTING

<160> NUMBER OF SEQ ID NOS: 1

<210> SEQ ID NO 1
<211> LENGTH: 1445
<212> TYPE: DNA
<213> ORGANISM: Streptomyces platensis

<400> SEQUENCE: 1
cctccttcgg gaggggatta gctggcgaac gggtgagtaa cacgtgggca atctgccctt    60
cactctggga caagccctgg aaacgggtc taatacccgg atacgacaca cgaccgcatg    120
gtctgtgtgt ggaaagctcc ggcggtgaag gatgagcccg cggcctatca gcttgttggt    180
ggggtgatgt cctaccaagg cgacgacggg tagccggcct gagagggcga ccggccacac    240
tgggactgag acacggccca gactcctacg ggaggcagca gtggggaata ttgcacaatg    300
ggcgaaagcc tgatgcagcg acgccgcgtg agggatgacg gccttcgggt tgtaaacctc    360
tttcagcagg gaagaagcga gagtgacggt acctgcagaa gaagcgccgg ctaactacgt    420
gccagcagcc gcggtaatac gtagggcgca agcgttgtcc ggaattattg ggcgtaaaga    480
gctcgtaggc ggcttgtcac gtcggatgtg aaagcccggg gcttaacccc gggtctgcat    540
tcgatacggg caggctagag ttcggtaggg gagatcggaa ttcctggtgt agcggtgaaa    600
tgcgcagata tcaggaggaa caccggtggc gaaggcggat ctctgggccg atactgacgc    660
tgaggagcga aagcgtgggg agcgaacagg attagatacc ctggtagtcc acgccgtaaa    720
cgttgggaac taggtgtggg cgacattcca cgtcgtccgt gccgcagcta acgcattaag    780
ttccccgcct ggggagtacg gccgcaaggc taaaactcaa aggaattgac gggggcccgc    840
acaagcagcg gagcatgtgg cttaattcga cgcaacgcca aagaaccttac caaggcttg    900 acatacaccg gaaacgtctg gagatcaggc gcccccttgt gtccggtgta tcatggtggt    960
```

```
-continued gcatggctgt cgtcagctcg tgtcgtgaga tgttggggtt taaktccccg caacgagcgc   1020 aaccottgtt ctgtgttgcc agcatgccct tcggggtgat ggggactcac aggagactgc   1080
cggggtcaac tcggaggaag gtggggacga cgtcaagtca tcatgcccct tatgtcttgg   1140
gctgcacacg tgctacaatg gccggtacaa tgagctgcga taccgcgagg tggagcgaat   1200
ctcaaaaagc cggtctcagt tcggattggg gtctgcaact cgaccccatg aagtcggagt   1260
tgctagtaat cgcagatcag cattgctgcg gtgaatacgt tcccgggcct tgtacacacc   1320
gcccgtcacg tcacgaaagt cggtaacacc cgaagccggt ggcccaaccc cttgtgggag   1380
ggaatcgtcg aaggtgggac tggcgattgg gacgaagtcg taacaaggta gccgtaccgg   1440
aaggt                                                              1445
```